(12) United States Patent
Rockwell et al.

(10) Patent No.: US 11,596,325 B2
(45) Date of Patent: Mar. 7, 2023

(54) SYSTEMS AND METHODS FOR MONITORING END TIDAL CARBON MONOXIDE

(71) Applicants: Jeffrey J. Rockwell, Edwards, CO (US); Mark L. Berrier, Austin, TX (US)

(72) Inventors: Jeffrey J. Rockwell, Edwards, CO (US); Mark L. Berrier, Austin, TX (US)

( * ) Notice: Subject to any disclaimer, the term of this patent is extended or adjusted under 35 U.S.C. 154(b) by 193 days.

(21) Appl. No.: 16/284,964

(22) Filed: Feb. 25, 2019

(65) Prior Publication Data

US 2019/0183384 A1 Jun. 20, 2019

Related U.S. Application Data

(63) Continuation of application No. 16/111,152, filed on Aug. 23, 2018, now abandoned.

(60) Provisional application No. 62/803,561, filed on Feb. 10, 2019, provisional application No. 62/577,273, filed on Oct. 26, 2017.

(51) Int. Cl.
| | | |
|---|---|---|
| *A61B 5/083* | (2006.01) | |
| *A61B 5/00* | (2006.01) | |
| *A61M 16/00* | (2006.01) | |
| *A61M 16/04* | (2006.01) | |
| *A61M 16/08* | (2006.01) | |
| *A61B 5/097* | (2006.01) | |
| *A61M 16/01* | (2006.01) | |

(52) U.S. Cl.
CPC ............ *A61B 5/0836* (2013.01); *A61B 5/097* (2013.01); *A61B 5/682* (2013.01); *A61M 16/0003* (2014.02); *A61M 16/0493* (2014.02); *A61M 16/085* (2014.02); *A61M 16/01* (2013.01); *A61M 2202/0208* (2013.01); *A61M 2205/3327* (2013.01)

(58) Field of Classification Search
None
See application file for complete search history.

(56) References Cited

U.S. PATENT DOCUMENTS

| | | | |
|---|---|---|---|
| 7,278,420 B2 | 10/2007 | Ganesh | |
| 8,413,658 B2 | 4/2013 | Williams | |
| 2001/0012923 A1* | 8/2001 | Christopher | ...... A61M 16/0488 604/48 |
| 2004/0129272 A1 | 7/2004 | Ganesh | |
| 2006/0042631 A1* | 3/2006 | Martin | ................ A61B 5/0836 128/207.18 |
| 2006/0118120 A1* | 6/2006 | Russo | ............... A61M 16/0488 128/207.14 |
| 2006/0272647 A1 | 12/2006 | Hauge | |

(Continued)

*Primary Examiner* — Jay B Shah

(57) ABSTRACT

Systems and methods for measurement of end tidal carbon dioxide, including a device having a body and a tubular gas line. The body is adapted to be attached to a patient airway and has a first gas line securing portion which has an aperture through it and is adapted to secure the gas line to the body. The tubular gas line is secured in the aperture. The tubular gas line has a proximal portion extending from a proximal end of the aperture and has a proximal end which is adapted to be connected to an end tidal CO2 monitor. The tubular gas line also has a distal portion extending from a distal end of the aperture and having a distal end which provides an inlet for end tidal CO2 exhaled by a patient.

16 Claims, 10 Drawing Sheets

(56) References Cited

U.S. PATENT DOCUMENTS

| | | | |
|---|---|---|---|
| 2010/0132700 A1* | 6/2010 | Filipi | A61B 1/00154 |
| | | | 128/200.26 |
| 2010/0326435 A1 | 12/2010 | Filipi | |
| 2012/0143003 A1 | 6/2012 | Anca | |
| 2013/0014754 A1 | 1/2013 | Guerra | |
| 2014/0024960 A1 | 1/2014 | Smith | |
| 2014/0081084 A1 | 3/2014 | Domenico | |
| 2014/0323896 A1 | 10/2014 | McCauley | |
| 2015/0013672 A1* | 1/2015 | Abdoue | A61M 16/0495 |
| | | | 128/200.26 |
| 2015/0265792 A1* | 9/2015 | Goudra | A61B 1/00154 |
| | | | 600/115 |
| 2017/0049985 A1* | 2/2017 | Salcedo | A61M 16/085 |

* cited by examiner

SYSTEMS AND METHODS FOR MONITORING END TIDAL CARBON MONOXIDE

CROSS-REFERENCE TO RELATED APPLICATIONS

This application is a continuation of U.S. patent application Ser. No. 16/111,152, filed Aug. 23, 2018, which claims the benefit of U.S. Provisional Patent Application 62/577,273, filed Oct. 26, 2017. This application also claims the benefit of U.S. Provisional Patent Application 62/803,561, filed Feb. 10, 2019. All of the foregoing patent applications are incorporated by reference as if set forth herein in their entirety.

BACKGROUND

Field of the Invention

The invention relates generally to end tidal carbon dioxide monitoring, and more specifically to systems and methods for performing end tidal carbon dioxide (CO2) monitoring with standard and modified oral airways to facilitate airway and anesthesia during medical procedures.

Related Art

End tidal carbon dioxide monitoring has become the standard in anesthetic and airway management. In 2011 the American Society of Anesthesiologists (ASA) issued a new mandate regarding end tidal CO2 monitoring, amending their monitoring standards. The ASA's new mandate states that during moderate or deep sedation, the adequacy of ventilation shall be evaluated by the continual observation of qualitative signs and monitoring for the presence of exhaled carbon dioxide.

Measurement of the patient's end tidal CO2 can provide an anesthesiologist with valuable patient information. An adequate level of CO2 provides assurance that the patient's airway is patent, provides a rough estimate of cardiac output, provides information about depth of anesthesia, and allows the anesthesiologist to gauge narcotic doses. It is therefore important to ensure that end tidal CO2 is reliably monitored.

It is easy and standard practice to monitor end tidal gases during general anesthetics utilizing advanced practice airways (endotrachial tubes or laryngeal mask airways), but anesthetics done under deep intravenous (IV) sedation without an advanced airway may, in many cases, impede or prevent monitoring of end tidal CO2, or may require the anesthesiologist to improvise and use creative techniques to enable CO2 monitoring. For example, it is not uncommon for practitioners to creatively tape CO2 monitoring lines to a face mask or nasal cannula. These gas lines are then connected to electronic monitoring devices that measure the level of CO2 being exhaled by the patient.

The results of these makeshift monitoring systems are cumbersome and provide poor quality CO2 measurements. Often, the quality of the CO2 monitoring is poor because of the poor location of the tubing and the resulting oxygen "washout" of end tidal gas. In other words, the oxygen that is provided to the patient may dilute (washout) the CO2, so that the level of CO2 cannot be reliably measured.

SUMMARY OF THE INVENTION

The systems and methods described herein provide solutions to these and other problems and enable the convenient and reliable measurement of end tidal carbon dioxide for surgical patients. The described CO2 detection systems include improved oral airways and devices that are attachable to standard, conventional oral airways to provide properly positioned conduits for CO2 monitoring as well as, in some embodiments, conduits for providing oxygen to the patient. In an exemplary embodiment, A CO2 gas line and potentially an oxygen supply line are mounted on an attachment plate that can be secured to the flange of a standard oral airway. When the attachment plate is secured to the flange, the CO2 gas line extends approximately ¼-⅓ of the way into the proximal end of the passageway through the oral airway, and is beveled at its distal end to decrease oxygen washout of the measured end tidal CO2. when used, the oxygen supply line extends substantially to the distal end of the passageway. The CO2 gas line and the oxygen line have connectors at their proximal ends to allow them to be connected to CO2 monitoring equipment and oxygen supplies, respectively.

One embodiment is a device that comprises a body and a tubular gas line. The body is adapted to be attached to a patient airway and has a first gas line securing portion which has an aperture through it and is adapted to secure the gas line to the body. The tubular gas line is secured in the aperture. The tubular gas line has a proximal portion extending from a proximal end of the aperture and has a proximal end which is adapted to be connected to an end tidal CO2 monitor. The tubular gas line also has a distal portion extending from a distal end of the aperture and having a distal end which provides an inlet for end tidal CO2 exhaled by a patient. In one embodiment, the body has a front plate, so that when the device is secured to the patient airway, the front plate is positioned against a proximal face of the patient airway. A layer of adhesive may be provided on the distal side of the front plate to adhere the distal side of the front plate to the proximal face of the patient airway and thereby secure the device to the patient airway. The front plate may, for example, be generally planar with an oval annular shape that is substantially the same shape as a front flange of the patient airway. The gas line securing portion may extend into a central opening in the oval annular front plate so that when the device is secured to the patient airway, the distal portion of the tubular gas line extends into the central passageway of the patient airway. The distal end of the tubular gas line may be tapered (e.g. at an angle of 30-60 degrees) with respect to the axis of the tubular gas line. The body may have a second gas line securing portion which is adapted to secure a second gas line (e.g., an oxygen line) to the body.

Another embodiment is adapted to be secured to a bite block airway. In this embodiment, the device has a body which includes a front plate and a separation wall which is connected to the front plate. When the device is secured to the bite block, the separation wall extends into a central passageway of the bite block and partitions the central passageway into a first, larger portion and a second, smaller portion. The distal portion of the tubular gas line is positioned in the second portion of the central passageway, thereby isolating it from the first portion of the central passageway. The separation wall isolates the distal portion of the tubular gas line from contact with instruments that are inserted into the first portion of the central passageway. This embodiment may use adhesive on the separation wall in order to adhere the separation wall to the interior of the central passageway. Alternatively, the front plate may be secured (e.g., adhered) to the face of the airway.

Another embodiment comprises a patient airway that has a device as described above which is attached to the airway.

Another embodiment comprises a method for providing a conduit in a patient airway to monitor end tidal CO2. The method includes providing an attachment body which has a conduit therethrough. The attachment body is secured to a patient airway so that a distal portion of the conduit is secured in a predetermined position with respect to the patient airway. The patient airway is positioned in a patient's mouth, and the proximal end of the conduit is coupled to a CO2 monitor, and end tidal CO2 which is exhaled by the patient is conveyed through the conduit to the CO2 monitor, where the end tidal CO2 is measured.

Numerous alternative embodiments are also possible.

BRIEF DESCRIPTION OF THE DRAWINGS

Other objects and advantages of the invention may become apparent upon reading the following detailed description and upon reference to the accompanying drawings.

Figure 1:
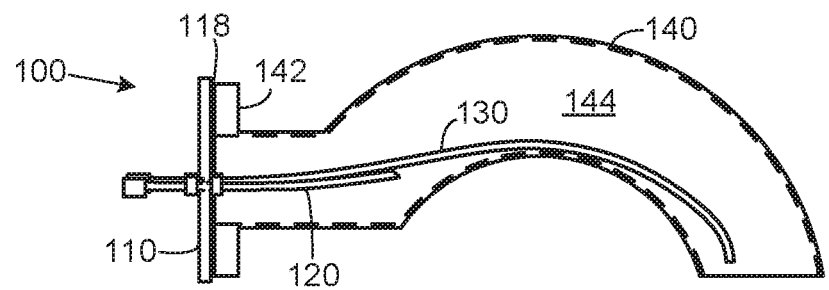
FIG. 1 is a diagram illustrating a CO2 detection device installed on a standard oral airway in accordance with a first embodiment.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims. Further, the drawings may not be to scale, and may exaggerate one or more components in order to facilitate an understanding of the various features described herein.

DETAILED DESCRIPTION OF EXEMPLARY EMBODIMENTS

One or more embodiments of the invention are described below. It should be noted that these and any other embodiments described below are exemplary and are intended to be illustrative of the invention rather than limiting.

As described herein, various embodiments of the invention comprise systems and methods for CO2 detection, wherein a CO2 gas line is installed on a conventional oral airway. One embodiment that provides a potential solution to the problems described above is the Tru-Cap oral airway adapter. The Tru-Cap oral airway adapter is based on a standard oral airway which is modified to have a standard luer lock connector (female) that attaches to a standard end tidal CO2 gas line (via a male luer lock). The CO2 gas line extends from a flange of the oral airway through a first port in the airway so that the distal intake orifice of the CO2 gas line is positioned within the airway's proximal section. The orifice is tapered to capture primarily gas exhaled by the patient. By placing intake orifice of the CO2 gas line in this position, it is possible to obtain a more accurate assessment of the patient's end tidal CO2, as compared to positions that are closer to the distal section of the oral airway, or at the flange of the airway. The resulting tracing of the CO2 is much more like that of an advanced airway, allowing the practitioner to make more accurate judgments of patient status based on CO2 monitoring. An additional port is provided in the airway for placement of oxygen tubing. This allows oxygen to be supplied to the patient in cases in which it is not possible or practical to use a face mask or nasal cannula. The exit orifice for the oxygen tubing is at the distal end of the airway in order to help prevent CO2 tracing "washout".

The present systems and methods are used to position a conduit with respect to a patient airway so that the conduit is properly positioned to enable consistent, effective monitoring of end tidal CO2. In some embodiments, the conduit is a small plastic tube that is inserted through a hole in an attachment body that is secured to a patient airway. In other embodiments, the conduit is integral to the attachment body, rather than being a separate piece that is installed in the attachment body. In some embodiments, the attachment body is substantially rigid (i.e., not necessarily completely inflexible, but nearly inflexible), while in others it is flexible to enable the body to conform more closely to the patient airway to which it is or will be attached.

The use of the devices described herein should have many applications in the operating room, as well as potential applications in patients who are in a post anesthesia care unit when recovering from a general anesthetic. The designs are simple, easy to use, easy to manufacture, and can bridge gaps in current CO2 monitoring capabilities. The devices are especially useful for cases in which moderate or deep sedation techniques are used.

Figure 2:
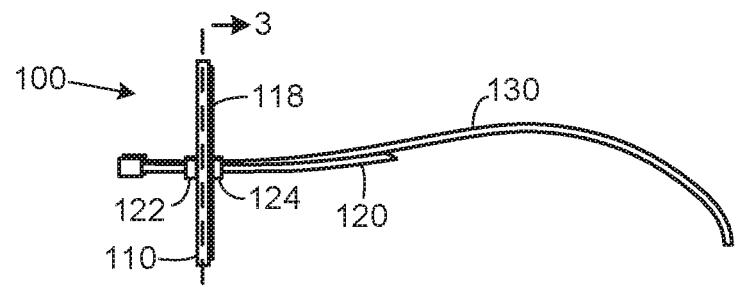
FIG. 2 is a diagram illustrating the CO2 detection device of the first embodiment prior to installation on a standard oral airway.
Figure 3:
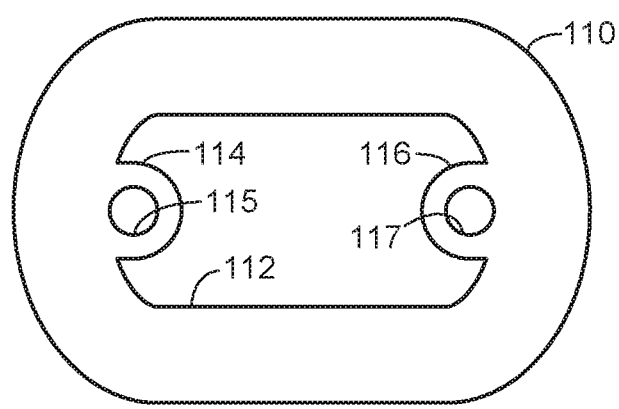
FIG. 3 is a diagram illustrating the configuration of an attachment plate of the CO2 detection device of the first embodiment.

Referring to FIGS. 1-3, a set of diagrams illustrate a first embodiment of a CO2 detection device that can be installed on a standard oral airway (a oropharyngeal airway). FIG. 1 is a side view of the device installed on a standard oral airway. FIG. 2 is a side view of the device prior to installation on the standard oral airway. FIG. 3 is a front view of a front plate or attachment plate of the device.

As used herein, the term "airway" or "patient airway" refers to a device that is inserted into a patient's mouth and/or throat in order to maintain a passageway through which the patient breathes. These airways may include, without limitation, oropharyngeal airways, nasopharyngeal airways, bite block airways, and the like.

In this embodiment, the device 100 is an apparatus that is retrofitted to a standard oral airway 140 to quickly and easily provide properly positioned gas lines for monitoring CO2 and, if desired, supplying oxygen to a patient. The apparatus includes an attachment plate 110 which holds a CO2 gas line 120 and, as depicted in the figure, an oxygen gas line 130. Each of the gas lines is secured to attachment plate 110. Attachment plate 110 is secured to oral airway 140 so that gas lines 120 and 130 are held securely within, and at the sides of, the passageway 144 through the oral airway.

Figure 5:
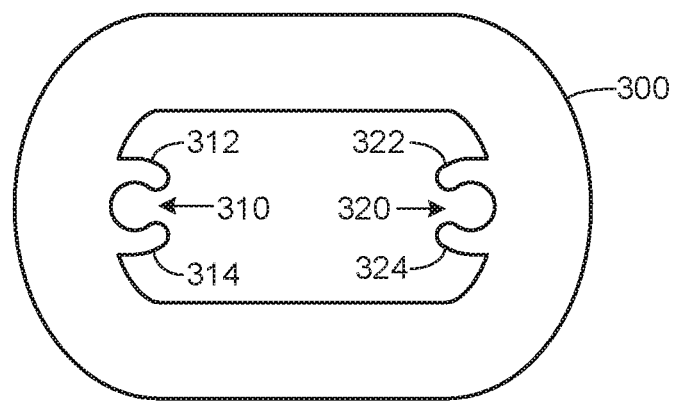
FIG. 5 is a diagram illustrating a second alternative configuration of an attachment plate for a CO2 detection device.
Figure 6:
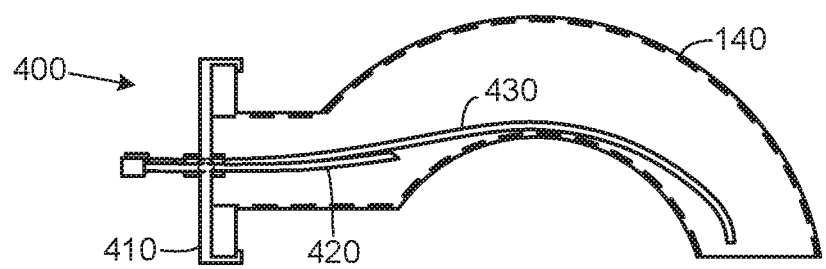
FIG. 6 is a diagram illustrating a CO2 detection device installed on a standard oral airway in accordance with a second embodiment.
Figure 7:
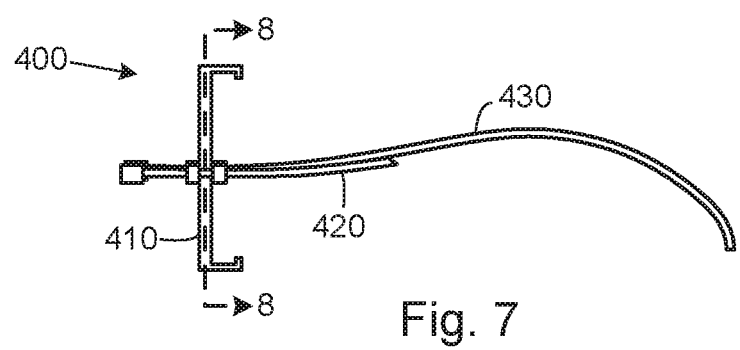
FIG. 7 is a diagram illustrating the CO2 detection device of the second embodiment prior to installation on a standard oral airway.
Figure 8:
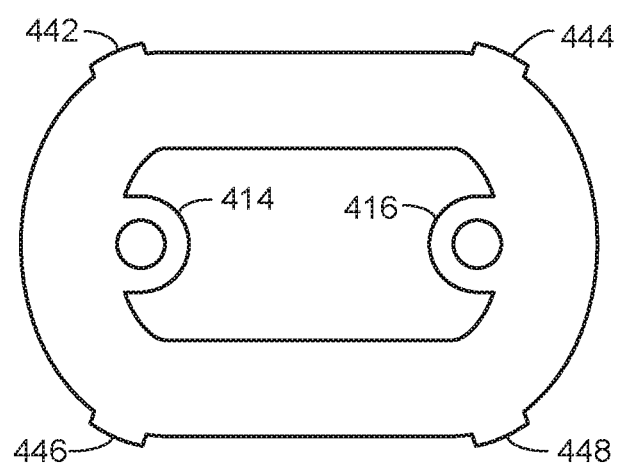
FIGS. 8 and 9 are diagrams illustrating the configuration of an attachment plate of the CO2 detection device of the second embodiment.

As shown in FIG. 3, attachment plate 110 has a generally oval shape, with a large, generally oval opening or aperture 112 through its center. The outer periphery of attachment plate 110 is approximately the same shape as the outer periphery of flange 142 of oral airway 140. Similarly, aperture 112 through attachment plate 110 is generally the same shape as the opening in flange 142 of oral airway 140. Attachment plate 110 does, however, have two gas-line-securing portions 114, 116 which extend inward, into the oval area of aperture 112. Each of these gas-line-securing portions (114, 116) of attachment plate 110 has a smaller, corresponding aperture (115, 117) through it. As used herein, the term "aperture" includes apertures or openings that are not completely enclosed, such as the opening that is formed between the arms (e.g., 312, 314) of a clip as shown in FIG. 5

CO2 gas line 120 is inserted through one of the gas-line-securing portions (e.g., 116), while oxygen gas line 130 is inserted through the other (e.g., 114). Gas lines 120 and 130 are held in place within gas-line-securing portions 114 and 116 in this embodiment by corresponding anchors (e.g., CO2 gas line 120 is secured by anchors 122 and 124). In alternative embodiments, the gas lines may be held in place by a simple friction-fit within the gas-line-securing portions, they may be glued in place, or they may be held in place by other means. A standard luer lock connector 126 is secured to the proximal end of CO2 gas line 120 to allow it to be connected to a CO2 monitoring system. Similarly, a luer lock connector is secured to oxygen gas line 130 to allow it to be connected to an oxygen supply. In alternative embodiments, other types of connectors can be provided to allow the gas lines to be connected to appropriate monitoring devices and oxygen sources. While the length of the gas lines (e.g., between anchor 122 and leer lock 126) is depicted as being relatively short in the figures, this portion of the gas lines may have any suitable length. It is contemplated that longer lengths may be more easily coupled to the inputs of electronic measurement devices.

In the embodiment of FIGS. 1-3, attachment plate 110 is secured to flange 142 of oral airway 140 by a layer of adhesive 118. Device 100 may initially be provided with a removable layer of paper or other material covering adhesive layer 118. The layer of paper protects adhesive layer 118 until the practitioner is ready to install the device on an oral airway. When the device is to be installed, the paper layer is removed, exposing adhesive layer 118. The device is then positioned with gas lines 120 and 130 extending through the opening in flange 142 and into the passageway 144 through oral airway 140, and with attachment plate 110 aligned with flange 142. Attachment plate 110 is then pressed against flange 142 so that adhesive layer 118 contacts flange 142 and bonds attachment plate 110 to flange 142.

Gas lines 120 and 130 extend to predetermined lengths past attachment plate 110, so that they are properly positioned within passageway 144 of oral airway 140 when device 100 is installed on the oral airway. Preferably, CO2 gas line 120 extends between one fourth and one third of the way into passageway 144, while oxygen gas line 130 extends almost the entire length of the passageway. Because the distal end of oxygen supply line 130 is positioned near the distal end of oral airway 140, oxygen which is supplied to the patient from this gas line does not washout the CO2 at the distal end of CO2 gas line 120, which is positioned closer to the proximal opening of the oral airway at flange 142. It should be noted that the distal end of CO2 gas line 120 may be tapered, so that the opening more directly faces the direction from which the exhaled CO2 is received. The tapering of the distal end of CO2 gas line 120 increases the accuracy and consistency of the CO2 measurement. "Tapered", as used herein, means that the face of the opening is not perpendicular to the axis of the gas line, but is instead angled (e.g., by 30-60 degrees, and preferably 45 degrees). The axis is at the center of the passageway through the gas line and coaxial with the gas line.

The CO2 gas line is adapted to be connected to an end tidal CO2 monitor. Electronic end tidal CO2 monitors are commonly found in hospitals and surgical centers (e.g., in operating rooms, intensive care units and the like). The designs and structures of these CO2 monitors is beyond the scope of this disclosure. The CO2 gas line may be connected directly to an end tidal CO2 monitor, or it may be coupled to the CO2 monitor via intermediate tubing or other means.

Figure 4:
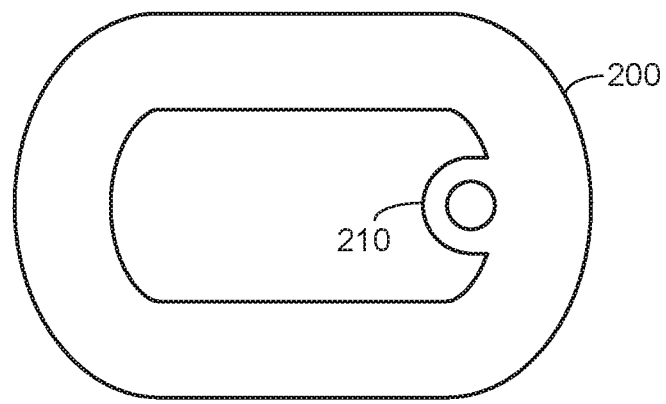
FIG. 4 is a diagram illustrating an alternative configuration of an attachment plate for a CO2 detection device.

While the embodiment described above uses the attachment plate configuration illustrated in FIG. 3, other configurations may be used in alternative embodiments. For example, FIGS. 4 and 5 illustrate two alternative configurations of the attachment plate. In the embodiment of FIG. 4, only a single gas-line-securing portion 210 is provided on attachment plate 200. This configuration would allow a single one of the gas lines (preferably the CO2 gas line) to be secured to the attachment plate. In the embodiment of FIG. 5, attachment plate 300 has two gas-line-securing portions 310 and 312, thereby allowing both the CO2 gas line and the oxygen gas line to be secured to the attachment plate. This is similar to the configuration of FIG. 3, but each of the gas-line-securing portions consists of two opposing extensions (312/314 or 322/324) which partially encircle the respective gas lines, rather than completely encircling them. This allows the gas lines to be "snapped" into place between the extensions and may facilitate installation of the gas lines. Still other alternative embodiments are possible, and may use these or other suitable combinations of gas-line-securing portions.

Figure 9:
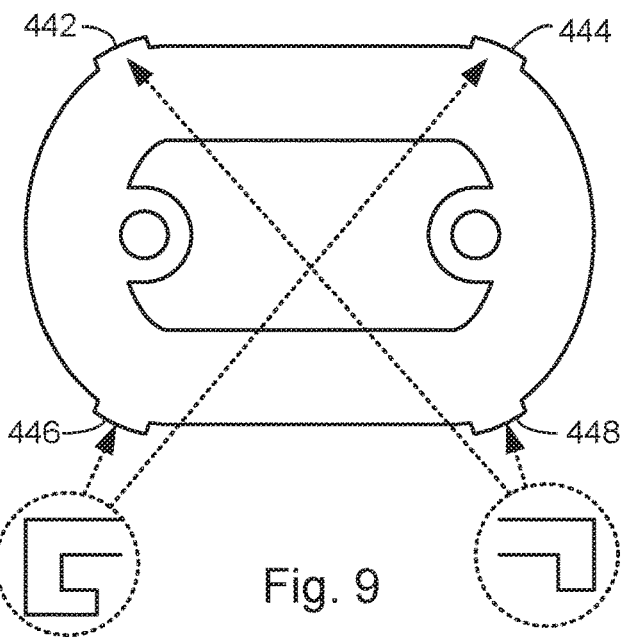
Figure 10:
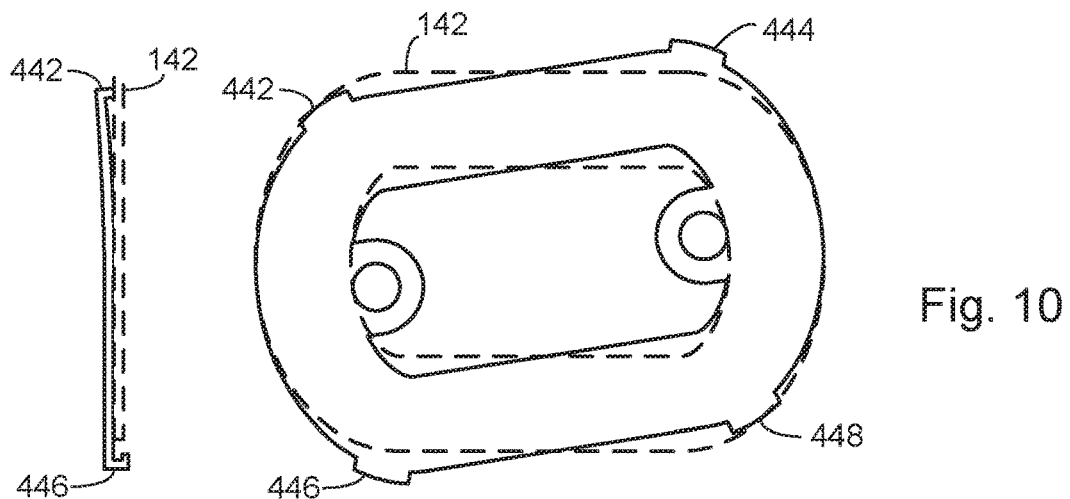
FIGS. 10 and 11 are diagrams illustrating the manner in which the attachment plate of the second embodiment of the CO2 detection device is secured to the flange of an oral airway.
Figure 11:
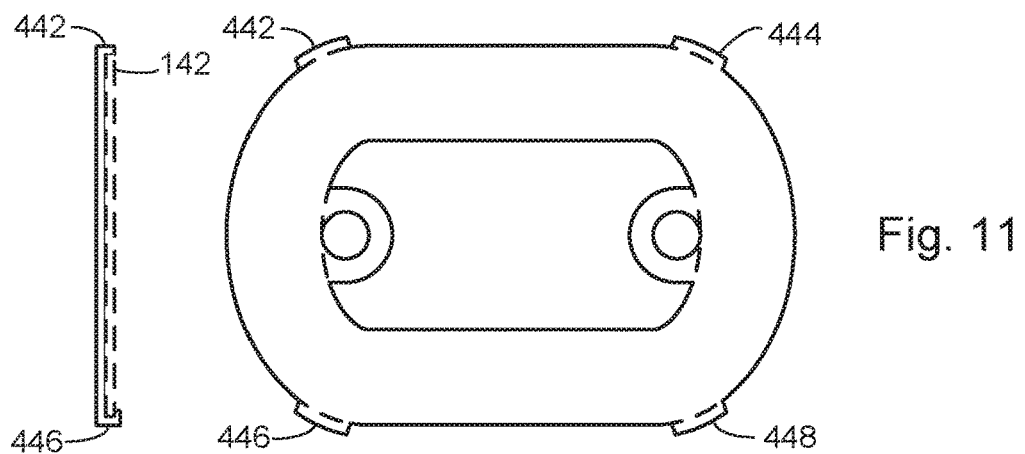

Referring to FIGS. 9-11, an alternative embodiment of the device is shown. In this embodiment, device 400 again has an attachment plate 410 that has a generally oval shape matching the flange of the standard airway, with two gas lines (420, 430) secured to it via gas-line-securing portions (414, 416). In this embodiment, however, attachment plate 410 is configured to be "clipped on" to the flange of the oral airway, rather than being adhered to it. This is achieved by providing tabs (442, 444, 446, 448) around the periphery of attachment plate 410. The structure of the tabs in this embodiment is illustrated in FIG. 9. It can be seen that tabs 444 and 446 have a portion that allows them to hook around the edge of the oral airway flange, while tabs 442 and 448 simply extend forward, toward the flange. This configuration allows the attachment plate to be placed against the oral airway flange and twisted to lock that attachment plate onto the flange.

The action of securing the attachment plate to the oral airway flange is illustrated in FIGS. 10 and 11. In FIG. 10, attachment plate 410 is placed flat against the face of flange 142, with the attachment plate rotated slightly with respect to the flange. In this position, the hooked tabs (444, 446) are positioned outward from the edge of the flange, while tabs 442 and 448 are positioned against the face of the flange. Attachment plate 410 flexes slightly to accommodate the positions of tabs 442 and 448 against the face of the flange, as shown at the left of FIG. 10. When attachment plate 410 is rotated slightly clockwise to align the generally oval periphery of the attachment plate with the generally oval outer periphery of flange 142, tabs 444 and 446 are hooked around the edge of flange 142, and tabs 442 and 448 spring forward (as shown in FIG. 11), locking attachment plate 410 in place against flange 142.

Figure 12:
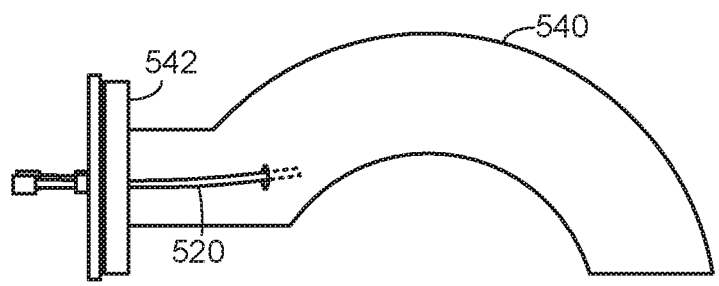
FIGS. 12-14 are diagrams illustrating a CO2 detection device installed on a modified oral airway in accordance with a third embodiment.
Figure 13:
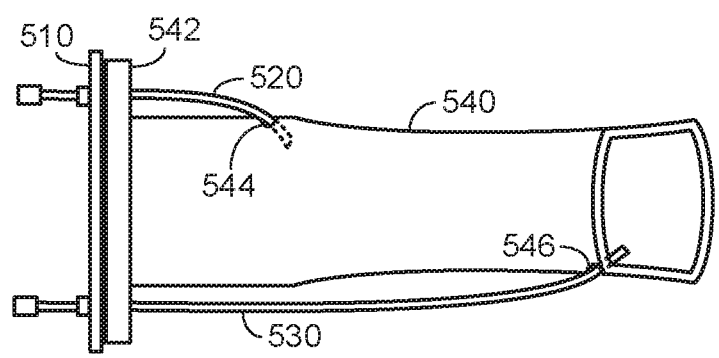
Figure 14:
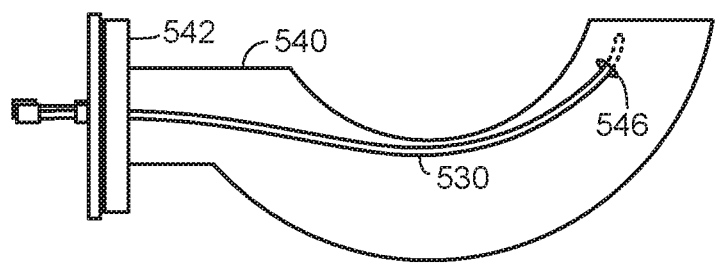

Referring to FIGS. 12-14, another alternative embodiment is shown. In this embodiment, the device includes not only attachment plate 510 and gas lines 520 in 530, but also oral airway 540. It can be seen that, in this embodiment, each of the gas lines extends through the attachment plate 510 and/or flange 542, along the exterior of the oral airway, and then through corresponding small apertures (544, 546) in the sides of the airway, so that the distal ends of the gas lines are positioned within the passageway of the oral airway. Attachment plate 510 may be adhered to or clipped onto flange 542, or the attachment plate may be formed integrally with the flange.

Figure 15:
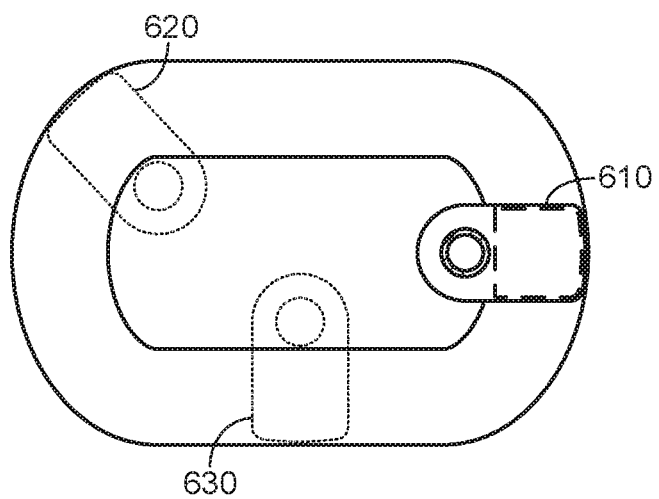
FIG. 15 is a diagram illustrating a CO2 detection device installed on a modified oral airway in accordance with a fourth embodiment.

Referring to FIG. 15, another alternative embodiment is shown. In this embodiment, the device uses an alternative configuration of an attachment plate to hold the CO2 and/or gas lines that extend into the oral airway. The configuration of the overall device is very similar to the embodiment of FIGS. 1-3, but the attachment plate 610 in this embodiment is smaller than plate 110 and only covers a portion of the flange of the oral airway. Attachment plate 610 is affixed to the flange using a layer of adhesive (shown by the dashed line), although clip-on or other attachment means could be used. While attachment plate 610 is depicted as being positioned at the right edge of the flange in FIG. 15, the smaller size of the attachment plate allows it to be affixed to other locations on the flange, such as in the corner (as indicated by dotted outline 620) or in the middle (as indicated by dotted outline 630) of the passageway. The smaller size of attachment plate 610 may make the device less costly to manufacture and store than if the larger attachment plate 110 is used.

Figure 16:
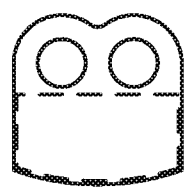
FIGS. 16-18 are diagrams illustrating alternative configurations of an attachment plate of the CO2 detection device of the fourth embodiment.
Figure 17:
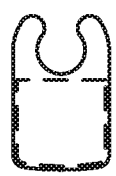
Figure 18:
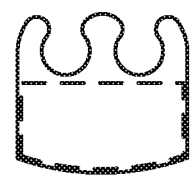

Referring to FIGS. 16-18, several alternative configurations of the smaller attachment plate are shown. FIG. 16 is a configuration having apertures through which two gas lines (CO2 and O2) can be inserted. FIG. 17 is a configuration that does not completely encircle the gas line, but instead allows the gas line to be clipped into the attachment plate. FIG. 18 is a configuration of the attachment plate that allows two gas lines to be clipped in and held by the attachment plate. Like the embodiment of FIG. 15, the attachment plates of FIGS. 16-18 can be secured to the flange of the oral airway using a layer of adhesive, clips, or the like. The attachment plates can be configured to hold one, two, or even more gas lines, and multiple attachment plates can be used in combination (e.g., two single-line attachment plates as shown in FIG. 15 or 17 can be attached to the oral airway flange to hold two gas lines). It should be noted that the attachment plate can have a variety of alternative shapes in addition to those shown and described above.

While the foregoing embodiments are used with an oral airway, some alternative embodiments are instead designed to be used with a bite-block type airway that is commonly used in endoscopic procedures. It is possible to use a device as described with an annular attachment plate, but the front face of the bite block is typically curved, so the distal side of the attachment plate may need to be curved as well, in order to be more easily attached (e.g., adhered) to the face of the bite block airway. The attachment plate may alternatively be attached to the bite block airway at specific points, rather than across the entire distal surface of the attachment plate in order to facilitate adhering it to the bite block airway.

Figure 19:
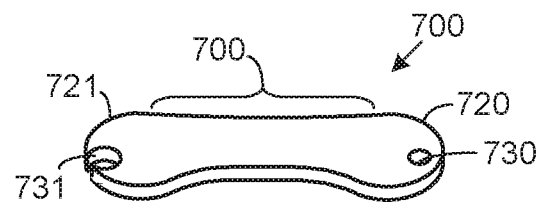
FIGS. 19-20 are diagrams illustrating an alternative embodiment of a CO2 detection device configured to be used with a bite block airway.
Figure 20:
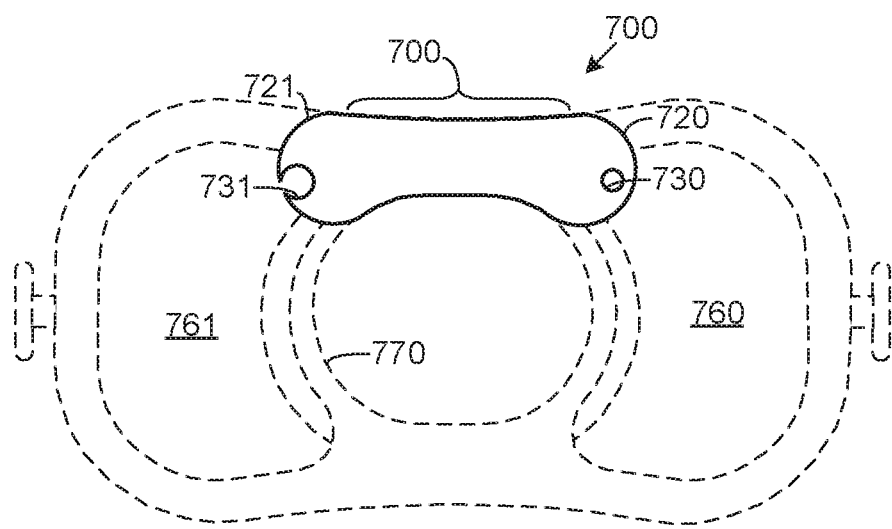

Another exemplary embodiment of a CO2 detection device configured to be used with a bite block airway (which may be referred to herein simply as a "bite block") is shown in FIGS. 19 and 20. FIG. 19 is a diagram illustrating an attachment plate of the device, and FIG. 20 is a diagram illustrating the attachment plate adhered to a bite block airway. The CO2 detection device may include CO2 and oxygen gas lines which are secured in the aperture of the attachment plate, but the gas lines are not shown here for purposes of clarity.

The device depicted in FIG. 19 includes an attachment plate 700 that extends across only a portion of the front face of bite block 750. The attachment plate is elongated so that it can be attached to the top of the bite block airway, which is one of the few parts of the illustrated bite block that is wide enough to allow the attachment plate to be affixed to it. Attachment plate 700 has a central portion 710 and two end portions 720 and 721. Because the front of the bite block airway is curved, an attachment plate having a flat rear surface may be difficult to adhere to the bite block airway. The attachment plate may therefore have a curved rear face in some embodiments which matches the curve of the front of the bite block airway. The attachment plate may be connected to the bite block airway by providing an adhesive layer on the rear face of the attachment plate, which allows the attachment plate to be adhered to the bite block airway in the same manner as the oral airway embodiments described above.

The end portions 720, 721 of attachment plate 700 overlap with openings 760 and 761 in the face of bite block airway 750. Apertures 730 and 731 are provided through end portions 720, 721 so that CO2 and oxygen gas lines (tubes) can be positioned within the apertures to secure them to the attachment plate. The gas lines may be secured by a friction fit within the apertures, or they may be made integral to the attachment plate. The gas lines extend along the exterior of a central tubular portion 770 through bite block airway 750, generally parallel to an axis of the tubular portion. The device will typically include a CO2 gas line which is secured within aperture 730. An oxygen gas line is may optionally be secured within aperture 731, which is open at the side to allow the oxygen line to be clipped into the aperture. This may facilitate installation of the oxygen line after the attachment plate is adhered to the front of the bite block airway. In one embodiment, the gas lines extend slightly beyond the posterior end of tubular portion 770. While the gas lines are not depicted in FIGS. 19 and 20, they would be installed and secured generally as shown and described in connection with the previous embodiments.

Figure 21:
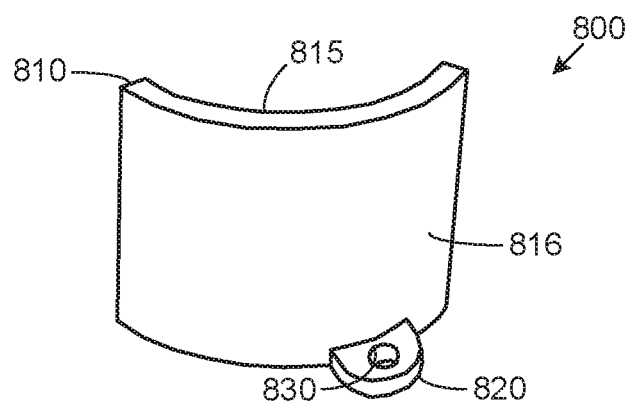
FIGS. 21-22 are diagrams illustrating another alternative embodiment of a CO2 detection device configured to be used with a bite block airway.
Figure 22:
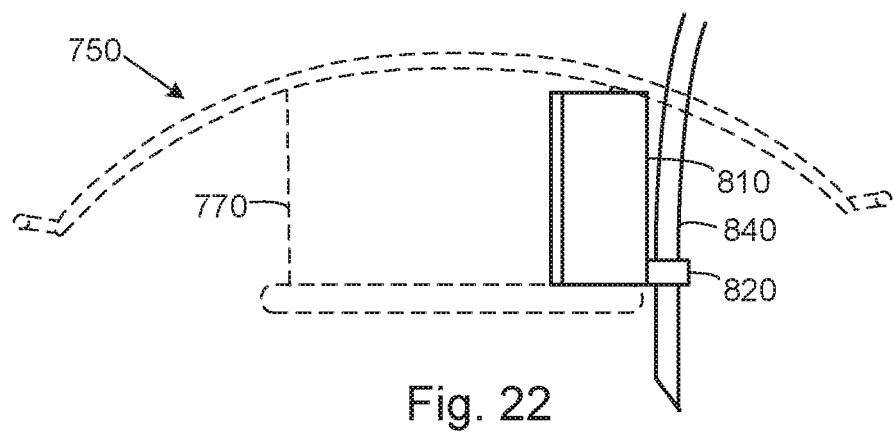

Another exemplary embodiment which is configured to be used with a bite block airway is shown in FIGS. 21 and 22. FIG. 21 is a diagram illustrating a perspective view of the device, FIG. 22 is a diagram illustrating the device adhered to a bite block airway. The bite block airway is illustrated using dashed lines. The device typically includes a CO2 gas line which is secured to the device, but the gas line is not shown in FIG. 21 for purposes of clarity, In this embodiment, device 800 has a curved attachment plate 810. A concave surface 815 of attachment plate 810 is designed to be complementary to the exterior surface of the tubular portion of the bite block to which it will be attached. An adhesive layer is provided on concave surface 815 to enable the device to be adhered to the exterior of the tubular portion of the bite block. The adhesive may cover the entirety of the concave surface, or only portions of the surface (e.g., strips of adhesive may be provided at opposite edges of the concave surface).

A gas line securing portion (tab) 820 protrudes from a convex surface 816 of attachment plate 810. Gas line securing portion 820 has an aperture 830 which extends through it. Aperture 830 is sized to allow a CO2 gas line 840 to be placed through the aperture. The gas line may, for instance, be secured by a friction fit within the aperture. It should be noted that, while the embodiment depicted in FIGS. 21 and 22 has only one tab in which a gas line can be installed, alternative embodiments may have additional, similarly structured tabs that can allow an oxygen gas line to be secured to the device as well. It may, however, be preferable to use separate devices for CO2 and oxygen lines in order to provide separation between the gas lines and reduce oxygen washout of the monitored CO2.

Figure 23:
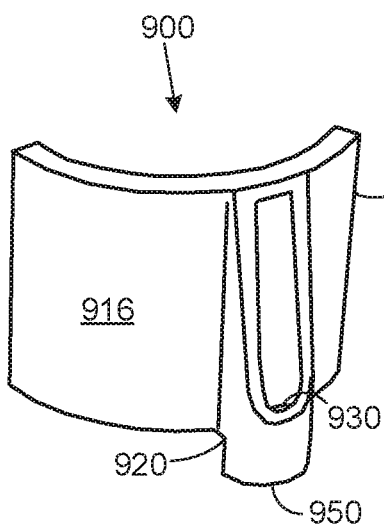
FIGS. 23-25 are diagrams illustrating another alternative embodiment of a CO2 detection device configured to be used with a bite block airway.
Figure 24:
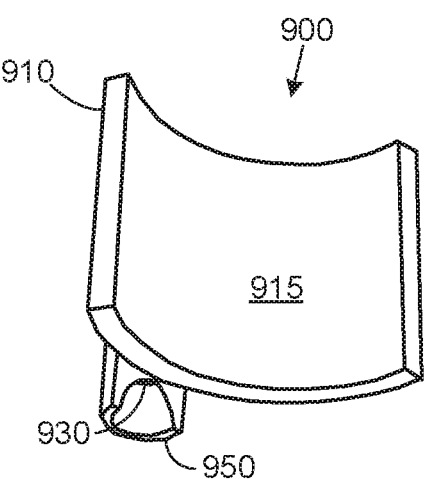
Figure 25:
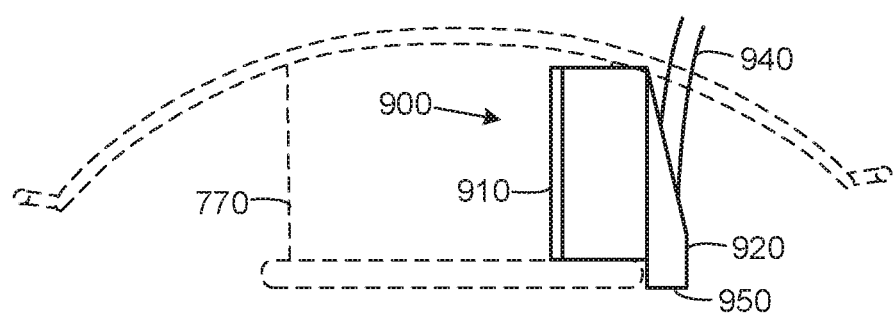

Referring to FIGS. 23-25, another alternative embodiment configured to be used with a bite block airway is shown. FIG. 23 is a diagram illustrating a perspective view from a convex side of the device, FIG. 24 is a diagram illustrating a perspective view from a concave side of the device, and FIG. 25 is a diagram illustrating the device adhered to a bite block airway (depicted by dashed lines). The device typically includes a CO2 gas line, but the gas line is not shown in FIGS. 23 and 24 for purposes of clarity.

In this embodiment, device 900 has a curved attachment plate 910, and an adhesive layer on concave surface 915 allows the device to be adhered to the exterior surface of the tubular portion of the bite block. A gas line securing portion 920 protrudes from convex surface 916 of attachment plate 910. Gas line securing portion 920 has an aperture 930 through it which is sized to allow a CO2 gas line 940 to be in the aperture and secured (e.g., by friction fit).

In the embodiment of FIGS. 23-25, gas line securing portion 920 forms a shroud 950 around the lower end of aperture 930. When gas line 940 is installed in aperture 930, it is positioned so that, rather than extending downward past the lower end of aperture 930 (as in the embodiment of FIG. 22), the opening of gas line 940 is positioned approximately even with the lower end of the aperture. Shroud 950 then serves to protect the opening of gas line 940 so that it is less likely to be clogged by the tissue of the tongue or throat, or substances in the patient's throat (e.g., lubricant that is typically used with an endoscope). In this embodiment, reinforcing ribs are provided to strengthen gas line securing portion 920 and shroud 950. As with the embodiment of FIGS. 23-25, additional gas line securing portions can be provided to allow an oxygen gas line to be secured to the device as well.

Figure 26:
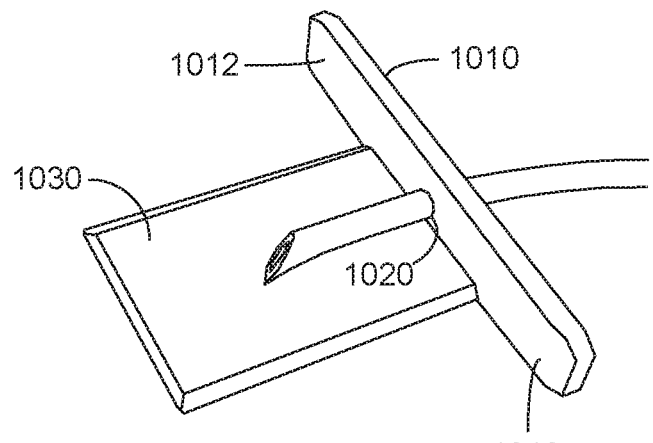
FIGS. 26-28 are diagrams illustrating additional alternative embodiments of a CO2 detection device configured to be used with a bite block airway.
Figure 27:
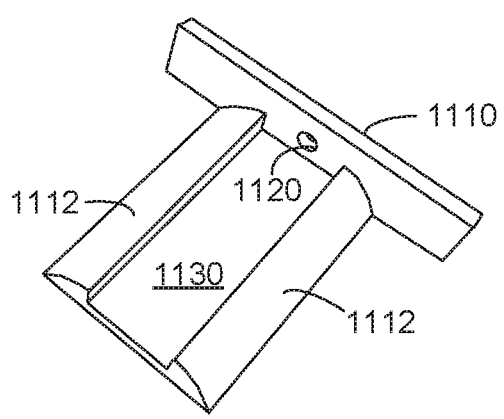

Referring to FIGS. 26-27, other alternative embodiments configured to be used with a bite block airway are shown. In contrast to the embodiments of FIGS. 21-25, both of these embodiments are designed to be installed on the interior of the central tubular portion through the bite block airway.

In each of the embodiments of FIGS. 26 and 27, the device (1000, 1100) has a front plate (1010, 1110) that is positioned against the front of the bite block airway. An aperture (1020, 1120) is provided through the front plate to enable installation of a gas line (e.g., 1040) to be secured in the front plate. A separation wall (1020, 1120) extends from the front plate, generally parallel to the gas line.

Figure 28:
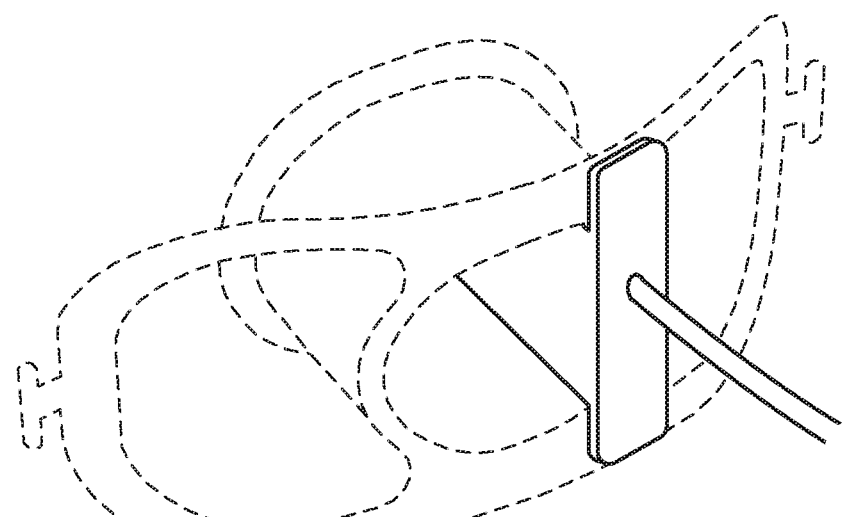

When the embodiments of FIGS. 26 and 27 are installed on a bite block airway (e.g., as shown in FIG. 28), the separation wall (1020, 1120) segregates or partitions the interior of the central tubular portion of the bite block airway into a first portion and a second portion. The first portion includes most of the volume within the central tubular portion, and is sufficiently large to allow an endoscope or other tool or instrument to be inserted through it. The second portion accommodates the gas line that is inserted through the front plate. The gas line may be positioned so that the opening at the end of the tube is located near the center of the separation wall (see, e.g., FIG. 26). Because the opening of the gas line is partially enclosed in the second portion of the interior of the central tubular portion of the bite block airway, the opening of the gas line is substantially protected from being clogged by any tissue or substance near the distal end of the bite block airway.

In the embodiment of FIG. 26, adhesive may be provided, e.g., on the distal side of front plate 1010 (i.e., at locations 1012). When the device is installed on the bite block airway, the adhesive adheres the device to the front of the bite block airway. In the embodiment of FIG. 27, adhesive may be provided at opposite edges of separation wall 1120. As depicted in the figure, the separation wall includes raised portions 1112 which are curved to match the interior surface of the central tubular portion of the bite block airway. Adhesive is provided on raised portions 1112 so that, when the device is installed on the bite block airway, the separation wall is adhered to the interior surface of the central tubular portion, thereby holding the device in place.

While the present invention has been described with reference to particular embodiments, it should be understood that the embodiments are illustrative and that the scope of the invention is not limited to these embodiments. Many variations, modifications, additions and improvements to the embodiments described above are possible. These alternative embodiments may include variations in the different features described above, such as the size and shape of the attachment plate, the number and configuration of the gas-line-securing portions of the attachment plate, the means for securing the attachment plate to the oral airway flange, the means for securing the gas lines to the attachment plate, and so on. It is contemplated that these variations, modifications, additions and improvements fall within the scope of the invention as detailed within the present disclosure.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the embodiments. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the described embodiment.

What is claimed is:

1. A system comprising:
   an oral airway having a tubular passageway adapted to be inserted into a patient's mouth in order to enable the patient to breathe through the passageway, the oral airway having a flange at a proximal opening of the tubular passageway;
   a body which is secured to the oral airway,
      wherein the body has a first gas line securing portion adapted to secure a gas line to the body, the first gas line securing portion having an aperture therethrough; and
   a tubular gas line secured in the aperture,
      the tubular gas line having a proximal portion extending from a proximal end of the aperture and having a proximal end adapted to be connected to an end tidal CO2 monitor,
      the tubular gas line having a distal portion extending from a distal end of the aperture and having a distal end which provides an inlet for end tidal CO2 exhaled by a patient;
   wherein the first gas line securing portion is positioned near a central opening through the body, thereby securing the tubular gas line in a position in which the distal portion of the tubular gas line extends into the central passageway of the oral airway
   wherein the oral airway comprises a bite block airway, the body having a separation wall connected thereto, wherein the separation wall extends into the central passageway of the bite block airway and partitions the central passageway, creating a first, larger portion and a second, smaller portion, wherein the distal portion of the tubular gas line is positioned in the second portion of the central passageway and wherein the distal end of the tubular gas line is physically separated by the separation wall from the first portion of the central passageway.

2. The system of claim 1, wherein the body comprises a front plate, wherein when the device is secured to the oral airway, the front plate is adjacent to a proximal face of the oral airway.

3. The system of claim 2, further comprising an adhesive positioned on a distal side of the front plate, wherein the adhesive secures a distal side of the front plate to the proximal face of the oral airway and thereby secures the device to the oral airway.

4. The system of claim 1, wherein the body is generally planar and has an oval annular shape which is substantially the same as a front flange of the oral airway.

5. The system of claim 4, wherein the first gas line securing portion of the body is configured to extend into a central opening in the oval annular front plate and wherein when the device is secured to the oral airway, the distal portion of the tubular gas line extends into a central passageway of the oral airway.

6. The system of claim 4, further comprising one or more tabs that are located around a periphery of the front plate, wherein the one or more tabs extend distally over an edge of the front flange of the oral airway, wherein the one or more tabs have corresponding hook portions that are adapted to clip the front plate onto the front flange of the oral airway.

7. The system of claim 1, further comprising an adhesive positioned on the body, wherein the adhesive is adapted to secure the body to the oral airway.

8. The system of claim 1, wherein the distal end of the tubular gas line is tapered with respect to an axis of the tubular gas line.

9. The system of claim 8, wherein a face of the distal end of the tubular gas line forms an angle of between 30 and 60 degrees with an axis of the tubular gas line.

10. The system of claim 1, wherein the body has a second gas line securing portion adapted to secure a second gas line to the body, the second gas line securing portion having an aperture therethrough.

11. The system of claim 10, wherein the front plate is generally planar and has a central opening therethrough corresponding to a front flange of the oral airway, wherein at least one of the first and second gas line securing portion has the aperture therethrough formed by two opposing extensions which partially encircle the aperture but do not completely encircle the aperture, thereby enabling gas lines to be snapped into place between the extensions from a position within the central aperture.

12. The system of claim 1, wherein the distal portion of the tubular gas line extends into the proximal end of the central passageway of the oral airway, and wherein the distal end of the tubular gas line is positioned between ¼ and ⅓ of a length of the central passageway from the proximal end of the central passageway.

13. The system of claim 1, wherein the separation wall prevents contact between the distal end of the tubular gas line and instruments positioned within the first portion of the central passageway.

14. A method for providing a conduit in an oral airway to monitor end tidal CO2, the method comprising:
   providing an oral airway having a tubular passageway adapted to be inserted into a patient's mouth in order to enable the patient to breathe through the passageway, the oral airway having a flange at a proximal opening of the tubular passageway, wherein the oral airway comprises a bite block airway, and wherein the body has a separation wall connected thereto;
   providing an attachment body, the attachment body having a conduit therethrough;
   securing the attachment body to the oral airway so that a distal portion of the conduit is secured in a predetermined position with respect to the oral airway, wherein the distal portion of the conduit extends through an opening at a proximal end of the oral airway and into a central passageway of the oral airway, wherein securing the attachment body to the oral airway comprises positioning the body with the separation wall extending into the central passageway of the bite block airway and partitioning the central passageway into a first, larger portion and a second, smaller portion, and positioning the distal portion of the tubular gas line in the second portion of the central passageway with the distal end of the tubular gas line physically separated by the separation wall from the first portion of the central passageway;
   positioning the oral airway in a patient's mouth; and
   coupling a proximal end of the conduit to a CO2 monitor.

15. The method of claim 14, further comprising: conveying end tidal CO2 exhaled by the patient into the central passageway of the oral airway and through the conduit to the CO2 monitor; and measuring the end tidal CO2 exhaled by the patient and conveyed through the central passageway of the oral airway and through the conduit.

16. The method of claim 14, wherein securing the distal portion of the conduit in the predetermined position comprises positioning the distal portion of the tubular gas line extending into the proximal end of the central passageway of the oral airway with the distal end of the tubular gas line positioned between ¼ and ⅓ of a Length of the Central passageway from the proximal end of the central passageway.

* * * * *